United States Patent [19]

Precopio

[11] Patent Number: 6,139,859
[45] Date of Patent: *Oct. 31, 2000

[54] METHODS AND COMPOSITIONS FOR TOPICAL TREATMENT OF ECTOPARASITES

[75] Inventor: Michael J Precopio, Collegeville, Pa.

[73] Assignee: Summers Laboratories, Inc., Collegeville, Pa.

[ * ] Notice: This patent is subject to a terminal disclaimer.

[21] Appl. No.: 09/131,862

[22] Filed: Aug. 10, 1998

Related U.S. Application Data

[63] Continuation of application No. 08/909,352, Aug. 11, 1997, Pat. No. 5,858,383.

[51] Int. Cl.$^7$ ..................................................... A01N 25/02
[52] U.S. Cl. ..................... 424/406; 424/70.1; 424/70.31; 424/78.02; 424/78.03; 424/78.08; 424/94.1; 424/405; 424/407
[58] Field of Search ..................................... 424/405, 406, 424/407; 70/70.1, 70.19, 70.31, 484, 485, 488, 94.1, 78.02, 78.03, 78.08

[56] References Cited

U.S. PATENT DOCUMENTS

| | | | |
|---|---|---|---|
| 4,379,168 | 4/1983 | Dotolo | 424/356 |
| 4,748,767 | 6/1988 | Sandels | 43/132.1 |
| 4,834,967 | 5/1989 | Locicero | 424/45 |
| 4,927,813 | 5/1990 | Bernstein | 514/65 |
| 5,211,941 | 5/1993 | Komori et al. | 424/70 |
| 5,462,556 | 10/1995 | Powers | 606/131 |
| 5,783,202 | 7/1998 | Tomlinson et al. | 424/405 |
| 5,858,383 | 1/1999 | Precopio | 424/405 |

OTHER PUBLICATIONS

Clear—Clear Lice Egg Remover Product Literature, Jun. 19, 1997.

Milks et al Practical Veterinary Pharmacology, Materia Medica & Therapeutics Alex Eger, Inc Chicago '49 pp. 350–353.

Bates—Pediatric News, Jun. 1997.

Merck p. 619 Limonene 1968.

*Primary Examiner*—Neil S. Levy
*Attorney, Agent, or Firm*—Henry E. Millson, Jr.

[57] ABSTRACT

Methods and compositions for the topical treatment of ectoparasites on animal skin utilizing a water-soluble or water-dispersible, substantially air-impermeable liquid composition.

20 Claims, No Drawings

METHODS AND COMPOSITIONS FOR TOPICAL TREATMENT OF ECTOPARASITES

This application is a continuation of prior application Ser. No. 08/909,352, filed Aug. 11, 1997, now U.S. Pat. No. 5,858,383.

FIELD OF THE INVENTION

This invention relates to methods and compositons for the topical treatment of animal skin infected with ectoparasites.

BACKGROUND OF THE INVENTION

Current methods for the treatment of ectoparasites, e.g. lice, utilize insecticidal compositions which are available in both prescription and over-the-counter formulations. Such compositions generally include one or more of the active ingredients benzyl benzoate, pyrethrin, permithrin, and lindane. Dispensing formulations include lotions, creams, shampoos, cream rinses, and gels.

However, increasing numbers of ectoparasite infections, especially head lice, that are resistant to the above insecticides have been reported in the medical literature.

Alternative insecticidal treatments such as the use of malathion, ivermectin, and a combination of trimethoprim and sulfamethazole have been tried, but usually only with mixed results.

Another approach that has been reported and which is effective is the use of topical petrolatum-containing products, which suffocate the parasites when left on the head overnight. However, removal of the petrolatum from the head and hair has proven to be a difficult problem, often taking about ten days for complete removal.

DESCRIPTION OF THE INVENTION

Other than in the operating examples, or where otherwise indicated, all numbers expressing quantities of ingredients used herein are to be understood as modified in all instances by the term "about".

It has now been discovered that ectoparasites on animal skin can be treated successfully by a method comprising the steps of A) applying to the skin affected by ectoparasites a water-soluble or water-dispersible, substantially air-impermeable liquid composition;

B) leaving the composition in contact with the skin until the ectoparasites have been killed; and C) removing the composition from the skin.

The present invention also relates to a composition for the treatment of ectoparasites and their nits on animal skin comprising I) water-soluble or water-dispersible, substantially air-impermeable liquid composition; and II) an effective quanitity of at least one substance that removes nits from skin and hair.

The ectoparasites treated by the methods and compostions of the invention include lice, especially the head louse and the crab (pubic) louse, and mites (chiggers, scabies and the like).

The animal skin treated by the methods of the present invention include any skin area infected by an ectoparasite, especially those covered by hair, such as the human scalp and pubic area. Also household pets and other animals infected by ectoparasites can also be treated by the methods of the invention.

The water-soluble or water-dispersible, substantially air-impermeable liquid composition used in the practice of the invention includes any such compositions that are compatible with the skin, i.e. that do not cause dermatitis, skin irritation, itching, or the like. These compositions can be anhydrous or may contain limited quantities of water. They can be specially formulated for use in the practice of the invention or can be selected from shampoos, shaving gels, pharmaceutical gels, hand lotions, and liquid hand dishwashing detergent compositions, provided they are or can be made to be substantially air impermeable. By substantially air-impermeable is meant that the composition does not contain sufficient air nor does it permit air to penetrate the composition in a quantity that would prevent the composition from suffocating the ectoparsites.

The compositions must also be water-soluble or water dispersible so that they can be readily removed by rinsing with water or other water-based liquid.

As stated above, the present compositions used in the method of the invention can be anhydrous or aqueous based. The compositions can be free-flowing or viscous; and preferably have a viscosity of at least about 1 centipoise at 20° C. The compositions can be homogeneous, or can be in the form of an oil-in-water or water-in-oil dispersion including in the form of a microemulsion. Also, O/W/O and W/O/W emulsions can be employed.

The components of the compositions and their quantities are not critical, provided the compositions can remain on the skin and successfully suffocate the ectoparasites.

The compositions preferably contain at least one skin-compatible surface active agent.

The skin-compatible surface active agents or mixture of such surface active agents can be selected from water soluble anionic, cationic, nonionic, polar nonionic, amphoteric, and zwitterionic surfactants, and soaps.

The compatible anionic surface active agents include those surface active or detergent compounds which contain an organic hydrophobic group containing generally 8 to 26 carbon atoms and preferably 10 to 18 carbon atoms in their molecular structure, and at least one water-solublizing group selected from the group of sulfonate, sulfate, carboxylate, phosphonate and phosphate so as to form a water-soluble detergent.

Examples of suitable anionic detergents which fall within the scope of the anionic detergent class include the water-soluble salts, e.g., the sodium, ammonium, and alkanolammonium salts, of higher fatty acids or resin salts containing about 8 to 20 carbon atoms, preferably 10 to 18 carbon atoms. Suitable fatty acids can be obtained from oils and waxes of animal or vegetable origin, e.g., tallow, grease, coconut oil, tall oil and mixtures thereof. Particularly useful are the sodium and potassium salts of the fatty acid mixtures derived from coconut oil and tallow, e.g., sodium coconut soap and potassium tallow soap.

The anionic class of detergents also includes the water-soluble sulfated and sulfonated synthetic detergents having an alkyl radical of 8 to 26, and preferably 12 to 22 carbon atoms, in their molecular structure.

The suitable anionic detergents include also $C_8$–$C_{18}$ acyl sarcosinates (e.g. sodium lauroyl sarcosinate), sodium and potassium salts of the reaction product of higher fatty acids containing 8–18 carbon atoms in the molecule esterified with isethionic acid, and sodium and potassium salts of the $C_8$–$C_{18}$ acyl N-methyl taurides, e.g., sodium cocoyl methyl taurate and potassium stearoyl methyl taurate.

Anionic phosphate surfactants in which the anionic solubilizing group is an oxyacid of phosphorous are also useful in the present compositions. Suitable phosphate surfactants are the sodium, potassium and ammonium alkyl phosphate esters. The compounds formed by including about one to 40 moles of ethylene oxide in the foregoing esters are also satisfactory.

The nonionic synthetic organic detergents are generally the condensation product of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a nonionic detergent. Further, the length of the polyethyleneoxy chain can be adjusted to achieve the desired balance between the hydrophobic and hydrophilic elements.

The nonionic detergents include the polyethylene oxide condensate of one mole of alkyl phenol containing from about 6 to 12 carbon atoms in a straight- or branched-chain configuration with about 5 to 30 moles of ethylene oxide, e.g., nonyl phenol condensed with 9 moles of ethylene oxide, dodecyl phenol condensed with 15 moles of ethylene oxide and dinonyl phenol condensed with 15 moles of ethylene oxide. Condensation products of the corresponding alkyl thiophenols with 5 to 30 moles of ethylene oxide are also suitable.

Still other suitable nonionics are the polyoxyethylene polyoxypropylene adducts of 1-butanol. The hydrophobe of these nonionics has a minimum molecular weight of 1,000 and consists of an aliphatic monohydric alcohol containing from 1 to 8 carbon atoms to which is attached a chain of oxethylene and oxypropylene. The weight ratio of oxypropylene to oxyethylene covers the range of 95:5 to 85:15. Attached to this is the hydrophilic polyoxyethylene chain which is from 44.4 to 54.6 percent of the total molecular weight of 1,400 to 4,000.

Also included in the nonionic detergent class are the condensation products of a higher alcohol containing about 8 to 18 carbon atoms in a straight or branched-chain configuration condensed with about 5 to 30 moles of ethylene oxide, e.g., lauryl-myristyl alcohol condensed with about 16 moles of ethylene oxide.

Other suitable nonionics may be derived by the condensation of ethylene oxide with the product resulting from the reaction of propylene oxide and ethylene diamine. The molecular weight varies from 500 to 4,500 or more.

Other nonionics that are especially compatible with the skin are the alkyl saccharide-type surface active agents represented by formula (I):

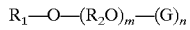

$$R_1-O-(R_2O)_m-(G)_n$$

wherein $R_1$ represents a linear or branched alkyl group of a $C_{8-18}$ carbon atom content, a linear or branched alkenyl group of a $C_{8-18}$ carbon atom content, or an alkylphenyl group of a $C_{8-18}$ carbon atom content, with the alkyl group being either linear or branched, $R_2$ represents an alkylene group of a $C_{2-4}$ carbon atom content, G represents a reduced sugar of a $C_{5-6}$ carbon atom content, m denotes a value of 0 to 10 and n denotes a value of 1 to 10.

Cationic surface active agents may also be employed. Such agents are those surface active detergent compounds which contain an organic hydrophobic group and a cationic solubilizing group. Typical cationic solubilizing groups are amine and quaternary groups.

Examples of suitable synthetic cationic detergents are normal primary amines $RNH_2$ wherein R is $C_{12}$–$C_{15}$; the diamines such as those of the type $RNHC_2H_4NH_2$ wherein R is an alkyl group of about 12 to 22 carbon atoms, such as N-2-aminoethyl stearyl amine and N-2-aminoethyl myristyl amine; amide-linked amines such as those of the type $R_1CONHC_2H_4NH_2$ wherein $R_1$ is an alkyl group of about 8 to 20 carbon atoms, such as N-2-amino ethylstearyl amide and N-amino ethylmyristyl amide; quaternary ammonium compounds wherein typically one of the groups linked to the nitrogen atom is an alkyl group of about 8–22 carbon atoms and three of the groups linked to the nitrogen atom are alkyl groups which contain 1 to 3 carbon atoms, including alkyl groups bearing inert substituents, such as phenyl groups, and there is present an anion such as halogen, acetate, methosulfate, etc. The alkyl group may contain intermediate linkages such as amido which do not substantially affect the hydrophobic character of the group, e.g., stearyl amido propyl quaternary ammonium chloride. Typical quaternary ammonium detergents are ethyldimethyl-stearyl ammonium chloride, benzyl-dimethyl-stearyl ammonium chloride, trimethyl-stearyl ammonium chloride, trimethyl-cetyl ammonium bromide, dimethyl-ethyl-lauryl ammonium chloride, dimethyl-propyl-myristyl ammonium chloride, and the corresponding methosulfates and acetates.

The amphoteric detergents which can be used in the compositions of this invention are generally water-soluble salts of derivatives of aliphatic amines which contain at least one cationic group, e.g. non-quaternary nitrogen, quaternary ammonium or quaternary phosphonium group, at least one alkyl group of 8–18 carbon atoms and may be straight chain or branched and the specific cationic atom may be part of a heterocyclic ring.

Zwitterionic surfactants include the betaines and sulfobetaines.

The polar nonionic detergents are those in which the hydrophilic group contains a semi-polar bond directly between two atoms, for example, N→O, P→O, and S→O. There is charge separation between the two directly bonded atoms, but the detergent molecule bears no net charge and does not dissociate into ions.

The polar nonionic detergents of this invention include open-chain aliphatic amine oxides of the general formula $R_1R_2R_3N{\rightarrow}O$. For the purposes of this invention $R_1$ is an alkyl, alkenyl, or monohydroxyalkyl radical having about 10 to 16 carbon atoms. $R_2$ and $R_3$ are each selected from the group consisting of hydrogen, methyl, ethyl, propyl ethanol, and propanol radicals.

Other operable polar nonionic detergents are the open-chain aliphatic phosphine oxides having the general formula $R_1R_2R_3P{\rightarrow}O$ wherein $R_1$ is an alkyl, alkenyl, or monohydroxyalkyl radical ranging in chain length from 10 to 18 carbon atoms, and $R_2$ and $R_3$ are each alkyl and monohydroxyalkyl radicals containing from 1 to 3 carbon atoms.

Soaps are the alkali metal, ammonium, or alkanolammonium salts of long chain fatty acids.

The concentration of surface active agents in the compositions used in the practice of the invention is not critical, as discussed above, but is usually in the range of from 5 to 85% by weight.

Other optional components of the present compositions include fillers, clays, lipophilic lower alkoxypolypropylene glycols having a molecular wight in the range of 1,000 to 2,500, such as butoxy polyoxypropylene glycols having a molecular weight of about 1,700; hydrophobic mixed polyethylene polyalkylene ($C_3$–$C_4$)glycol condensates of butanol having a molecular weight of about 400 to 4000 and containing from 35 to 65 percent by weight of polethylene glycol; polyhydric alcohols containing 2 to 3 carbon atoms such as glycerol and propylene glycol; and gums, such as gum tragacanth.

An optional but preferred component is one or more thickening agents such as cellulose derivatives, gelatin, agar, pectin, casein, alginates, acrylic polymers, polyurethane polymers, and high molecular weight polyethylene glycol. While the compositions preferably contain at least one surface active agent, compositions which do not contain a surface active agent can also be used in the practice of the invention. For example, a water-based pharmaceutically acceptable jelly can be used, such as jellies formulated with a whole gum or a powdered gum, e.g. gum tragacanth, acacia, chondrus, gelatin, carboxymethylcellulose, and the like, preferably containing a small quantity of a preservative, such as methyl p-hydroxybenzoate.

One particularly useful composition contains water, sodium alginate, glycerin, and calcium gluconate, in which the calcium ions cause cross-linking with sodium alginate to form a relatively firm gel.

Also, anhydrous compositions such as those based on glycerin or glycerides can also be used, as well as fish-liver oils, optionally diluted with vegetable oil.

In step A) of the present method, a coating of the composition is applied to the infected skin, either by hand or by a suitable applicator. In the case of head lice, the head is then covered with a suitable cover, such as a shower cap or bathing cap.

In step B), the composition is allowed to remain in contact with the scalp or other skin area until the parasites are dead, e.g. from 4 to 24 hours, preferably from 6 to 10 hours. An overnight period is usually adequate.

In step C), the composition is then readily removed, e.g. by rinsing with water.

The above treatment will kill all motile stages of lice, but the nits (eggs) are not easily destroyed, and hence repeat treatments will probably be necessary.

However, a composition of the invention can be used in the above method which will also effectively remove the nits as well as killing the ectoparasites. Component I) of the composition is the same water-soluble or water-dispersible, substantially air-impermeable liquid used in the above-described method of the invention. Component II) is one or more substances that remove nits, usually by loosening the adhesive bond that fastens the nits to the skin or hair. Such substances include formic acid, and enzymes that loosen the nits by differential hydration. Such enzymes include one or more of oxidoreductase, transferase, lyase, hydrolase, isomerase, and ligase. Concentrations of Component II) substances that are effective for removing nits depend on the particular substance chosen, but generally range from 0.0001 to 10% by weight of the composition. However, since formic acid can be caustic to the skin, when formic acid is used, the quantity of formic acid in the composition should be as small as possible, consistent with nit-removing effectiveness.

The above composition is then used in the method of the invention to remove both ectoparasites and nits from the affected area of animal skin.

The invention will be illustrated but not limited by the following examples.

EXAMPLES

Example 1 a) Preparation of composition without nit-removing component.

The following ingredients are blended together in a mixer:

| | |
|---|---|
| palmitic acid | 25 g. |
| triethanolamine | 14.5 g. |
| fatty acid esters | 20 g. |
| palmitamine oxide | 12 g. |
| sorbitol | 3.5 g. |
| lauryl alcohol | 5 g. |
| aloe vera gel | 10 g. |
| cellulose polymer | 5 g. |
| deionized water | 5 g |
| | 100 g. |

Example 2 a) Preparation of another composition without nit-removing component.

The following ingredients are blended together in a mixer

| | |
|---|---|
| cetearyl alcohol | 20 g. |
| keratin | 12 g. |
| stearalkonium chloride | 1 g. |
| panthenol | 6 g. |
| PEG 4000 | 24 g. |
| methylparaben | 0.5 g. |
| polysorbate 20 | 10 g. |
| tocopheryl acetate | 3 g. |
| potassium sorbate | 1.5 g |
| magnesium citrate | 15 g |
| deionized water | 7 g. |
| | 100 g. | b) application

The composition prepared above is applied by hand to a lice infected human scalp and covered with a shower cap. After about 8 hours the head is thoroughly rinsed with water. The lice are all killed and removed from the scalp with the rinse water.

Example 3

The composition of Example 1 is prepared and 10 grams of a mixture of 1 gram of a combination of oxidoreductase, transferase. lyase, hydrolase, isomerase, and ligase in 9 grams of water are added thereto and thoroughly mixed. The resulting composition is applied as in Example 1. Both the lice and the nits are effectively removed from the scalp and the hair.

What is claimed is:

1. A method for the topical treatment of lice and/or mites on animal skin comprising the steps of
   A) applying to the skin and hair containing the lice and/or mites a water-soluble or water dispersible, substantially air-impermeable, skin compatible liquid composition, wherein the liquid composition can range from free-flowing to viscous;
   B) leaving the composition in contact with the skin and hair until the lice and/or mites have been killed by suffocation; and
   C) removing the composition and the dead lice and/or mites from the skin and hair;

wherein in step B) suffocation is the only mechanism by which the composition kills the lice and/or mites.

2. The method of claim 1 wherein the composition also contains an effective quantity of at least one enzyme that loosens nits.

3. The method of claim 1 wherein in step C) the composition is removed by rinsing with water.

4. The method of claim 1 wherein the composition contains at least one skin compatible surface active agent selected from the group consisting of water-soluble anionic, cationic, nonionic, polar nonionic, amphoteric, and zwitterionic surfactants, and soaps.

5. The method of claim 4 wherein the composition also contains a thickening agent.

6. The method of claim 1 wherein the viscosity of the compostion is at least about 1 centipoise at 20° C.

7. The method of claim 1 wherein in step A) the composition is a water-based pharmaceutically acceptable jelly containing a gum.

8. The method of claim 1 wherein step B) the composition is left in contact with the skin and hair for from about 4 to about 24 hours.

9. The method of claim 8 wherein in step B) the composition is left on the scalp and hair for a period of from about 6 to about 10 hours.

10. A method for the topical treatment of the human scalp infected with head lice comprising the steps of A) applying to the scalp and hair a water-soluble or water-dispersible substantially air-impermeable, skin compatible, liquid composition, wherein the liquid composition can range from free-flowing to viscous;

B) leaving the composition on the scalp and hair until the lice have been killed by suffocation; and C) removing the composition and the dead lice from the scalp and hair;

wherein in step B) suffocation is the only mechanism by which the composition kills the lice.

11. The method of claim 10 wherein the composition also contains an effective quantity of at least one enzyme that loosens lice nits.

12. The method of claim 10 wherein in step B) the composition is left on the scalp and hair for a period of from about 4 to about 24 hours.

13. A method for the topical treatment of lice and/or mites on animal skin and hair comprising the steps of A) applying to the skin and hair containing lice and/or mites a water rinseable, substantially air impermeable barrier composition;

B) leaving the composition in contact with the skin and hair until the lice and/or mites have been killed by suffocation;

C) removing the composition and the dead lice and/or mites from the skin and hair;

D) applying to the skin and hair an effective quantity of at least one enzyme that loosens nits; and E) removing the at least one enzyme from the skin and hair together with the loosened nits.

14. The method of claim 13 wherein the animal skin and hair is the human scalp and the lice are head lice.

15. The method of claim 13 wherein the composition in step A) contains at least one skin compatible surface active agent selected from the group consisting of water-soluble, anionic, cationic, nonionic, polar nonionic, amphoteric and zwitterionic surfactants, and soaps.

16. The method of claim 13 wherein the composition in step A) also contains a thickening agent.

17. The method of claim 13 wherein the viscosity of the composition in step A) is at least about 1 centipoise at 20° C.

18. The method of claim 13 wherein in step A) the composition is a water-based pharmaceutically acceptable jelly containing a gum.

19. The method of claim 13 wherein in step B) the composition is left in contact with the skin and hair for from about 4 to about 24 hours.

20. The method of claim 13 wherein in step C) the composition is removed by rinsing with water.

* * * * *